(12) United States Patent
Nakakura et al.

(10) Patent No.: US 6,492,357 B1
(45) Date of Patent: Dec. 10, 2002

(54) COMPOSITIONS AND METHODS FOR CONTROLLING INSECTS WHICH DAMAGE RICE AND OTHER CROPS

(75) Inventors: Norihiko Nakakura, Tsukuba (JP); Philip R. Timmons, Durham, NC (US)

(73) Assignee: Aventis CropScience, S.A., Lyons (FR)

( * ) Notice: Subject to any disclaimer, the term of this patent is extended or adjusted under 35 U.S.C. 154(b) by 0 days.

(21) Appl. No.: 09/660,777

(22) Filed: Sep. 13, 2000

Related U.S. Application Data

(60) Provisional application No. 60/153,837, filed on Sep. 14, 1999.

(51) Int. Cl.[7] ................. A61K 31/535; A01N 43/56
(52) U.S. Cl. ..................... 514/229.2; 514/404
(58) Field of Search ............... 514/404, 229.2

(56) References Cited

U.S. PATENT DOCUMENTS

| | | | |
|---|---|---|---|
| 5,082,860 A | 1/1992 | Karrer et al. | 514/486 |
| 5,708,170 A | 1/1998 | Annis et al. | 544/212 |
| 5,716,977 A | 2/1998 | Colliot et al. | 514/407 |

FOREIGN PATENT DOCUMENTS

| | | |
|---|---|---|
| WO | 97/33476 | 9/1997 |
| WO | 98/39972 | 9/1998 |
| WO | 00/54591 | 9/2000 |

OTHER PUBLICATIONS

"Mixtures of Arthropodicides and Fungicides", *Research Disclosure*, No. 397, May 1997, pp. 361–363, XP000726479, published by Industrial Opportunities Ltd., Havant, GB.

*Primary Examiner*—Allen J. Robinson
(74) *Attorney, Agent, or Firm*—Burns, Doane, Swecker & Mathis, L.L.P.

(57) ABSTRACT

Compositions and methods for controlling insect populations, in particular, insects which attack rice crops, are disclosed. The compositions include one or more compounds from the Formula 1A and one or more compounds from the formulas 1B–G described in the specification, and optionally but preferably include a suitable carrier.

21 Claims, No Drawings

COMPOSITIONS AND METHODS FOR CONTROLLING INSECTS WHICH DAMAGE RICE AND OTHER CROPS

This application claims benefits of application Ser. No. 60/153,837 filed Sep. 14, 1999.

FIELD OF THE INVENTION

This invention is generally in the area of compositions and methods for controlling insects which damage rice and other crops. More particularly, this invention relates to pesticidal compositions comprising ethiprole and indoxacarb or structurally related compounds, and methods for using the compositions to treat rice crops for pests such as *Nilaparvata lugens* (brown planthoppers), *Cnaphalocrocis medinalis* (rice leaf rollers), and Nephotettix spp. (rice leaf hoppers), for example, *Nephotettix cincticeps* (green leaf hopper), the most common insects which attack rice crops.

BACKGROUND OF THE INVENTION

Rice crops are often attacked by pests such as Nephotettix spp. (rice leaf hoppers), such as *Nephotettix cincticeps* (green leaf hopper), *Nilaparvata lugens* (brown planthoppers) and *Cnaphalocrocis medinalis* (rice leaf rollers). Significant research efforts have been carried out to develop insecticidal compositions useful for controlling these pests.

It is very difficult to control insect pests which belong to Homoptera such as planthoppers, leafhoppers, aphids and whiteflies because of their specific ecological and physiological character traits and also due to the rapid development of drug-resistant insects. There are currently few methods to effectively control such insect pests.

U.S. Pat. No. 5,082,860 to Karrer, et al. discloses using ethyl 2-[4-(3,5-difluorophenoxy)phenoxy]ethylcarbamate to control cicadas which damage rice crops. However, it is unclear whether the carbamate is useful in treating green leaf hoppers, brown planthoppers and rice leaf rollers.

Frequently, several insecticides are effective against one or more of the above insects, but not all of them. Accordingly, the use of a single insecticide is often insufficient to protect crops of useful plants adequately against pests. For example, indoxacarb is not particularly effective against brown planthoppers, but is active against green leaf hoppers and rice leaf rollers.

It would be advantageous to provide new compositions and methods for controlling cicadas and other insects which damage rice and other crops. The present invention provides such compositions and methods.

SUMMARY OF THE INVENTION

Compositions and methods for controlling insect populations, in particular, insects which attack rice crops, are disclosed. The compositions include one or more compounds from the Formula 1A and one or more compounds from the formulas 1B–G, and optionally but preferably include a suitable carrier.

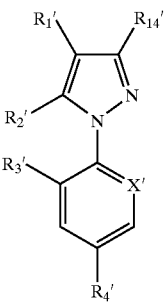

FORMULA 1A

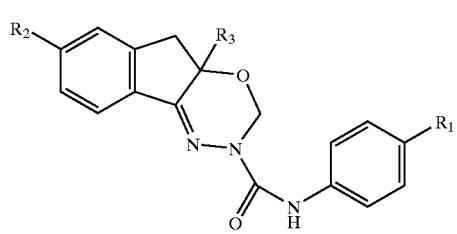

FORMULA 1B

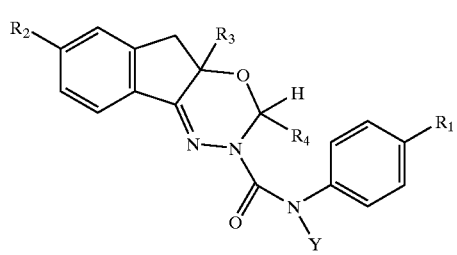

FORMULA 1C

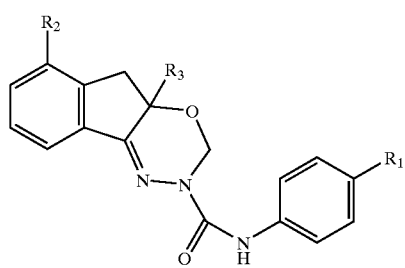

FORMULA 1D

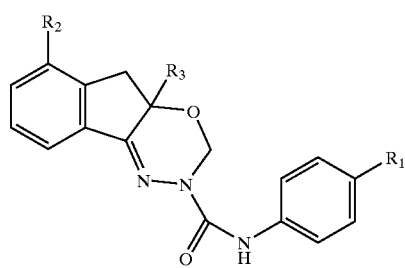

FORMULA 1E

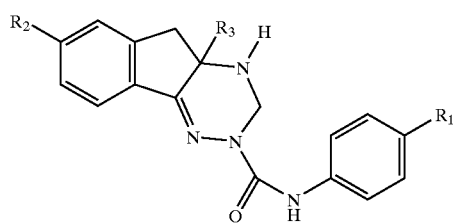

FORMULA 1F

FORMULA 1G

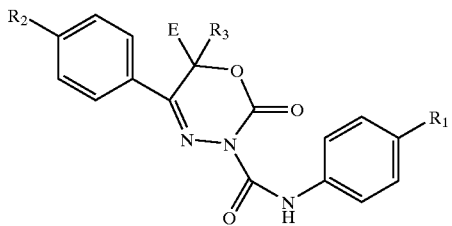

The compounds of Formula IA–G are intended to include all geometric and stereoisomers, agriculturally suitable salts thereof, agricultural compositions containing them and their use for the control of insects in both agronomic and non-agronomic uses. The term "compounds" will be understood to include all such isomers and salts thereof.

E is selected from the group H and $C_1$-$C_3$ alkyl; or

Y is selected from the group H; $C_1$-$C_6$ alkyl, benzyl; $C_2$-$C_6$ alkoxyalkyl; $C_2$-$C_6$ alkenyl; $C_2$-$C_6$ alkynyl; $C_1$-$C_6$ alkyl optionally substituted by halogen, $C_1$-$C_3$ alkoxy, $C_1$-$C_3$ haloalkoxy, —CN, —$NO_2$, $S(O)_rR^{32}$, $COR^{32}$, $CO_2R^{32}$, phenyl optionally substituted by halogen, —CN, $C_1$-$C_2$ haloalkyl and $C_1$-$C_2$ haloalkoxy; $C_3$-$C_6$ cycloalkyl; $C_3$-$C_6$ cyclohaloalkyl; $C_3$-$C_6$ cycloalkylalkyl; —CHO; $C_2$-$C_6$ alkylcarbonyl; $C_2$-$C_6$ alkoxycarbonyl; $C_2$-$C_6$ haloalkylcarbonyl; $COR^{36}$; $CO_2R^{36}$; $C_1$-$C_6$ alkylthio; $C_1$-$C_6$ haloalkylthio; phenylthio; $R^{12}OC(O)N(R^{13})S$— and $R^{14}(R^{15})NS$—;

$R^1$ and $R^2$ are independently selected from the group H, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_3$-$C_6$ haloalkynyl, $C_2$-$C_6$ alkylthioalkyl, $C_2$-$C_6$ alkylthioalky, $C_1$-$C_6$ nitroalkyl, $C_2$-$C_6$ cyanoalkyl, $C_3$-$C_8$ alkoxycarbonylalkyl, $C_3$-$C_6$ cycloalkyl, $C_3$-$C_6$ halocycloalkyl, halogen, —CN, —$N_3$, —SCN, —$NO_2$, —$OR^{17}$, —$SR^{17}$, —$S(O)R^{17}$, —$S(O)_2R^{17}$, —$OC(O)R^{17}$, —$OS(O)_2R^{17}$, —$CO_2R^{17}$, —$C(O)R^{17}$, —$C(O)NR^{17}R^{18}$, —$SO_2NR^{17}R^{18}$, —$NR^{17}R^{18}$, —$NR^{18}C(O)R^{17}$, —$OC(O)NHR^{17}$, —$NR^{18}C(O)NHR^{17}$, —$NR^{18}SO_2R^{17}$, phenyl optionally substituted with 1 to 3 substituents independently selected from W, and benzyl optionally substituted with 1 to 3 substituents independently selected from W; or when m or n is 2, $(R^1)_2$ can be taken together, or $(R^2)_2$ can be taken together as —$OCH_2O$—, —$OCF_2$ O—, —$OCH_2$ $CH_2$ O—, —$CH_2$ $C(CH_3)_2$ O—, —$CF_2$ $CF_2$ O or —$OCF_2$ $CF_2$ O— to form a cyclic bridge; provided that when $R^1$ or $R^2$ is $S(O)R^{17}$, $S(O)_2$ $R^{17}$, $OC(O)R^{17}$ or $OS(O)_2$ $R^{17}$ then $R^{17}$ is other than H;

$R^3$ is selected from the group H, J, —$N_3$, —$NO_2$, halogen, —$N(R^{22})R^{23}$, $C(R^{34})$=N—O—$R^{35}$, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ alkoxylalkyl, $C_3$-$C_8$ alkoxycarbonylalkyl, —$CO_2R^{17}$, —$OR^{19}$, —$C(O)R^{17}$, —$C(O)NR^{17}R^{18}$, —$C(S)NR^{17}R^{18}$, —$C(S)R^{17}$, —$C(S)SR^{17}$, —CN, —$Si(R^{28})(R^{29})R^{27}$, —$SR^{27}$, —$S(O)R^{27}$, —$SO_2R^{27}$, —$P(O)(OR^{27})_2$, phenyl, phenyl substituted with $(R^{16})_p$, benzyl and benzyl substituted with 1 to 3 substituents independently selected from W; or $R^3$ is $C_2$-$C_6$ epoxyalkyl optionally substituted with a group selected from $C_1$-$C_3$ alkyl, —CN, —$C(O)R^{24}$, —$CO_2R^{24}$ and phenyl optionally substituted with W; or $R^3$ is $C_1$-$C_6$ alkyl substituted with a group selected from —$C(O)N(R^{25})R^{26}$, —$C(O)R^{25}$, —$SR^{27}$, —$S(O)R^{27}$, —$SO_2R^{27}$, —SCN, —CN, $C_1$-$C_2$ haloalkoxy, —$Si(R^{28})(R^{29})R^{30}$, $N(R^{22})R^{23}$, $ONO_2$, —$OC(O)R^{25}$, —$P(O)(OR^{27})_2$ and J;

J is selected from the group saturated, partially unsaturated or aromatic 5- or 6-membered heterocyclic ring, bonded through carbon or nitrogen, containing 1–4 heteroatoms independently selected from the group consisting of 0–2 oxygen, 0–2 sulfur and 0–4 nitrogen, this substituent optionally containing one carbonyl and optionally substituted with one or more members selected from W;

$R^4$ is selected from the group H, $C_1$-$C_4$ alkyl, $COR^{20}$ and $C_2$-$C_4$ alkoxycarbonyl; or $R^{12}$ is $C_1$-$C_6$ alkyl;

$R^{13}$ is $C_1$-$C_4$ alkyl;

$R^{14}$ and $R^{15}$ are independently $C_1$-$C_4$ alkyl; or $R^{14}$ and $R^{15}$ can be taken together as —$CH_2CH_2CH_2CH_2CH_2$— or —$CH_2CH_2OCH_2CH_2$—;

$R^{16}$ is selected from the group $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_3$-$C_6$ haloalkynyl, $C_2$-$C_6$ alkoxyalkyl, $C_2$-$C_6$ alkylthioalky, $C_1$-$C_6$ nitroalkyl, $C_2$-$C_6$ cyanoalkyl, $C_3$-$C_8$ alkoxycarbonylalkyl, $C_3$-$C_6$ cycloalkyl, $C_3$-$C_6$ halocycloalkyl, halogen, CN, $N_3$, SCN $NO_2$, $OR^{17}$, $SR^{17}$, $S(O)R^{17}$, $S(O)_2$ $R^{17}$, $OC(O)R^{17}$, $OS(O)_2$ $R^{17}$, $CO_2$ $R^{17}$, $C(O)R^{17}$, $C(O)N$ $R^{17}$ $R^{18}$, $SO_2$ N $R^{17}$ $R^{18}$, N $R^{18}C(O)R^{17}$, $OC(O)NH$ $R^{17}$, N $R^{18}$ $C(O)NH$ $R^{17}$, N $R^{18}$ $SO_2$ $R^{17}$, phenyl optionally substituted with 1 to 3 substituents independently selected from W, and benzyl optionally substituted with 1 to 3 substituents independently selected from W; or when p is 2, $(R^{16})_2$ can be taken together as —$OCH_2O$—, —$OCF_2O$—, —$OCH_2$ $CH_2O$—, —$CH_2$ $C(CH_3)_2O$—, —$CF_2$ $CF_2O$ or —$OCF_2CF_2O$— to from a cyclic bridge; provided that when $R^{16}$ is $S(O)R^{17}$, $S(O)_2$ $R^{17}$, $OC(O)R^{17}$ or $OS(O)_2$ $R^{17}$ then $R^{17}$ is other than H;

$R^{17}$ is selected from the group H, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_3$-$C_6$ haloalkynyl, $C_2$-$C_6$ alkoxyalkyl, $C_2$-$C_6$ alkylthioal, $C_1$-$C_6$ nitroalkyl, $C_2$-$C_6$ cyanoalkyl, $C_3$-$C_8$ alkoxycarbonylalkyl, $C_3$-$C_6$ cycloalkyl, $C_3$-$C_6$ halocycloalkyl, and optionally substituted phenyl and benzyl wherein the substituents are 1 to 3 substituents independently selected from W;

$R^{18}$ is selected from the group H and $C_1$-$C_4$ alkyl; or $R^{17}$ and $R^{18}$, when attached to the same atom, can be taken together as —$(CH_2)_4$—, —$(CH_2)_5$—, or —$CH_2$ $CH_2$ $OCH_2$ $CH_2$—;

$R^{19}$ is selected from the group H, $C_1$-$C_4$ alkyl, $C_2$-$C_4$ alkenyl, $C_2$-$C_4$ alkynyl, $C_2$-$C_4$ alkylcarbonyl, $C_2$-$C_4$ alkoxycarbonyl and $C_1$-$C_4$ alkylsulfonyl;

$R^{20}$ is $C_1$-$C_3$ alkyl;

$R^{21}$ is selected from the group H, $C_1$-$C_4$ alkyl, $C_2$-$C_4$ alkenyl and $C_2$-$C_4$ alkynyl;

$R^{22}$ is selected from the group H, $C_2$-$C_7$ alkylcarbonyl, $C_2$-$C_7$ alkoxycarbonyl, optionally substituted $C_1$-$C_4$ alkyl, optionally substituted $C_2$-$C_4$ alkenyl, and optionally substituted $C_2$-$C_4$ alkynyl, the substituents selected from $C_1$-$C_2$ alkoxy, CN, $C(O)R^{30}$ and $C(O)_2$ $R^{27}$;

$R^{23}$ is selected from the group H, $C_1$-$C_3$ alkyl, phenyl, phenyl substituted with W, benzyl and benzyl substituted with W;

$R^{24}$ is selected from the group H, $C_1$-$C_4$ alkyl, $C_2$-$C_4$ alkenyl and $C_2$-$C_4$ alkynyl;

$R^{25}$ and $R^{26}$ are independently selected from the group H and $C_1$-$C_2$ alkyl;

$R^{27}$ is selected from the group $C_1$-$C_3$ alkyl, phenyl and phenyl substituted with W;

$R^{28}$ is $C_1$-$C_3$ alkyl;

$R^{29}$ is $C_1$-$C_3$ alkyl;

$R^{30}$ is selected from the group H, $C_1$-$C_3$ alkyl, phenyl and phenyl substituted by W;

$R^{32}$ is selected from the group $C_1$-$C_3$ alkyl;

$R^{34}$ is selected from the group H, Cl, $C_1$-$C_4$ alkyl, $C_1$-$C_4$ alkoxy, $C_1$-$C_2$ thioalkyl and CN;

$R^{35}$ is selected from the group H, $C_1$-$C_4$ alkyl, $C_2$-$C_3$ alkylcarbonyl and $C_2$-$C_3$ alkoxycarbonyl;

$R^{36}$ is selected from the group phenyl and phenyl substituted with W;

W is selected from the group halogen, CN, $NO_2$, $C_1$-$C_2$ alkyl, $C_1$-$C_2$ haloalkyl, $C_1$-$C_2$ alkoxy, $C_1$-$C_2$ haloalkoxy, $C_1$-$C_2$ alkylthio, $C_1$-$C_2$ haloalkylthio, $C_1$-$C_2$ alkylsulfonyl and $C_1$-$C_2$ haloalkylsulfonyl;

m is 1 to 3;
n is 1 to 3;
p is 1 to 3;
r is 0, 1 or 2;
t is 2 or 3; and
u is 1 or 2.

Exemplary values of J include:

[chemical structures]

$R^{1'}$ is $S(O)_m R^{5'}$;

$R^{2'}$ is selected from a hydrogen atom, a halogen atom, $-NR^{6'}R^{7'}$, $-S(O)_{n'}R^{8'}$, $C(O)R^{8'}$, $C(O)OR^{9'}$, alkyl, haloalkyl, $-OR^{9'}$, or $-N=C(R^{10'})(R^{11'})$;

$R^{3'}$ is selected from a halogen atom or the hydrogen atom;

$R^{4'}$ is selected from a halogen atom, haloalkyl, haloalkoxy, $-S(O)_{p'}CF_3$, or $-SF_5$;

$R^{5'}$ is alkyl or haloalkyl;

$R^{6'}$ and $R^{7'}$ are independently selected from a hydrogen atom, alkyl, haloalkyl, $-C(O) R^{8'}$, $C(O)OR^{8'}$, $-S(O)_{q'}CF_3$; the alkyl portions of which are optionally substituted by one or more $R^{12'}$; or $R^{6'}$ and $R^{7'}$ are joined so as together form a divalent radical having 4 to 6 atoms in the chain, this divalent radical being alkylene, alkyleneoxyalkylene or alkyleneaminoalkylene, preferably to form a morpholine, pyrrolidine, piperidine or piperazine ring;

$R^{8'}$ is alkyl or haloalkyl;

$R^{9'}$ is selected from alkyl, haloalkyl or the hydrogen atom;

$R^{10'}$ is selected from $R^{9'}$ or alkoxy;

$R^{11'}$ is alkyl or haloalkyl; or is selected from phenyl or heteroaryl that is optionally substituted by one or more groups selected from hydroxy, halogen, alkoxy, $-S(O)_r R^{8'}$, cyano, $R^{8'}$ or combinations thereof;

$R^{12'}$ is selected from cyano, nitro, alkoxy, haloalkoxy, $-S(O)_s$-alkyl, $-S(O)_s$-haloalkyl, $-C(O)$-alkyl, $-C(O)$-haloalkyl, $-C(O)O$-alkyl, $-C(O)O$-haloalkyl, aminocarbonyl, alkylaminocarbonyl, dialkylaminocarbonyl, hydroxy, aminosulfonyl, alkylaminosulfonyl or dialkylaminosulfonyl;

X' is selected from the nitrogen atom, or the radical C-$R^{13'}$;

$R^{13'}$ is a halogen atom;

$R^{14'}$ is $-C(O)CH_3$ or $-CN$; and m', n', p', q', r' and s' represent, independently of one another, the values zero, one or two;

Unless otherwise specified alkyl and alkoxy groups have from one to eight, preferably one to four carbon atoms. The haloalkyl and haloalkoxy groups likewise preferably have one to four carbon atoms. The various individual aliphatic hydrocarbon moieties, that is, radicals and portions thereof (for example the alkyl moiety of alkylaminocarbonyl and alkylaminosulfonyl) have up to four carbon atoms in the chain.

The haloalkyl and haloalkoxy groups can bear one or more halogen atoms.

The term heteroaryl refers to a five to seven membered heterocyclic ring containing from one to four heteroatoms selected from nitrogen, oxygen and sulfur.

The term halogen means F, Cl, Br or I. The term "halo" before the name of a radical means that this radical is partially or completely halogenated, that is to say, substituted by F, Cl, Br or I, in any combination, preferably by F or Cl.

$R^{2'}$ is preferably an amino group, which is unsubstituted or which bears one or two substituents selected from the group consisting of alkyl, $-C(O)R^{8'}$ and $-C(O)OR^{8'}$; the alkyl portions of which are optionally substituted by one or more $R^{12'}$.

$R^{3'}$ is preferably a halogen atom; especially preferred is a chlorine atom;

$R^{4'}$ is preferably selected from a halogen atom, haloalkyl, haloalkoxy, or $-SF_5$; especially preferred are $CF_3-$, $CF_3O-$ and $-SF_5$.

$R^{5'}$ is preferably methyl, ethyl or propyl.

A particularly preferred group of compounds of general formula (I) because of their systemic aphicidal properties are those wherein:

$R^{2'}$ is $NR^{6'}R^{7'}$;
$R^{3'}$ is halogen;
$R^{4'}$ is $CF_3-$, $CF_3-$ or $-SF_5$;
$R^{5'}$ is alkyl;
X is $CR^{13'}$;
$R^{13'}$ is halogen; and
m' is 0 or 1.

Preferred compounds are those wherein:

$R^1$ is selected from the group H, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_3$-$C_6$ haloalkynyl, $C_2$-$C_6$ alkoxyalkyl, $C_2$-$C_6$ alkylthioal, $C_1$-$C_6$ nitroalkyl, $C_2$-$C_6$ cyanoalkyl, $C_3$-$C_6$ alkoxycarbonylalkyl, $C_3$-$C_6$ cycloalkyl, $C_3$-$C_6$ halocycloalkyl, halogen, CN, SCN, $NO_2$, O $R^{17}$, S $R^{17}$, $SO_2$ $R^{17}$, $CO_2$ $R^{17}$, $C(O)R^{17}$, phenyl optionally substituted with 1 to 3 substituents independently selected from W, and benzyl optionally substituted with 1 to 3 substituents independently selected from W; with one $R^1$ substituent in the 4-position, or when m is 2 then $(R^1)_2$ can be taken together as —$CH_2$ $C(CH_3)_2$ O—, —$OCH_2$ $CH_2O$—, —$OCF_2$ $CF_2O$—, or —$CF_2$ $CF_2O$— to form a 5- or 6-membered fused ring;

$R^2$ is selected from the group H, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_3$-$C_6$ haloalkynyl, $C_2$-$C_6$ alkoxyalkyl, $C_2$-$C_6$ alkylthioal, $C_1$-$C_6$ nitroalkyl, $C_2$-$C_6$ cyanoalkyl, $C_3$-$C_8$ alkoxycarbonylalkyl, $C_3$-$C_6$ cycloalkyl, $C_3$-$C_6$ halocycloalkyl, halogen, CN, SCN, $NO_2$, O $R^{17}$, S $R^{17}$, $S(O)_2$ $R^{17}$, $OC(O)R^{17}$, $OS(O)_2$ $R^{17}$, $CO_2$ $R^{17}$, $C(O)R^{17}$, $C(O)N$ $R^{17}$ $R^{18}$, $SO_2NR$ $R^{18}$, N $R^{17}$ $R^{18}$, phenyl optionally substituted with 1 to 3 substituents independently selected from W, and benzyl optionally substituted with 1 to 3 substituents independently selected from W;

$R^3$ is selected from the group H, $C_1$-$C_4$ alkyl, $C_3$-$C_4$ alkoxycarbonylalkyl, $CO_2$ $R^{17}$, $C(O)R^{17}$, phenyl and phenyl substituted by $(R^{16})_p$;

$R^{16}$ is selected from the group $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_3$-$C_6$ haloalkynyl, $C_2$-$C_6$ alkoxyalkyl, $C_2$-$C_6$ alkylthioal, $C_1$-$C_6$ nitroalkyl, $C_2$-$C_6$ cyanoalkyl, $C_3$-$C_8$ alkoxycarbonylalkyl, $C_3$-$C_6$ cycloalkyl, $C_3$-$C_6$ halocycloalkyl, halogen, CN, SCN, $NO_2$, O $R^{17}$, S $R^{17}$, $S(O)_2$ $R^{17}$, $OC(O)R^{17}$, $OS(O)_2$ $R^{17}$, $CO_2$ $R^{17}$, $C(O)R^{17}$, $C(O)N$ $R^{17}$ $R^{18}$, $SO_2$ N $R^{17}$ $R^{18}$, N $R^{17}$ $R^{18}$, phenyl optionally substituted with 1 to 3 substituents independently selected from W, and benzyl optionally substituted with 1 to 3 substituents independently selected from W;

$R^{17}$ is selected from the group $C_1$-$C_4$ alkyl, $C_1$-$C_2$ haloalkyl, $C_3$-$C_4$ alkenyl and propargyl;

$R^{18}$ is selected from the group H and $CH_3$;

m is 1 or 2;

n is 1 or 2; and p is 1 or 2.

Additional preferred compounds include those wherein $R^{2'}$ is $NR^{6'}R^{7'}$;

$R^{3'}$ is chlorine;

$R^{4'}$ is $CF_3$—, $CF_3O$— or —$SF_5$;

$R^{5'}$ is alkyl;

$R^{6'}$ is hydrogen;

$R^{7'}$ is hydrogen,—$S(O)_qCF_3$, or alkyl optionally substituted by —$S(O)_sR^{8'}$ or aminocarbonyl;

X is $CR^{13'}$;

$R^{13'}$ is chlorine or bromine; and m' is 0 or 1.

A further particularly preferred class of compounds of general formula (I) because of their systemic aphicidal properties are those wherein:

$R^{2'}$ is $NR^{6'}R^{7'}$;

$R^{3'}$ is chlorine;

$R^{4'}$ is $CF_3$— or —$SF_5$;

$R^{5'}$ is methyl or ethyl;

$R^{6'}$ is hydrogen;

$R^{7'}$ is hydrogen, methyl or ethyl optionally substituted by —$S(O)_sR^{8'}$ or aminocarbonyl;

$R^{8'}$ is methyl or ethyl;

$R^{9'}$ is methyl or ethyl;

X is $CR^{13'}$;

$R^{13'}$ is chlorine or bromine; and m' is 0 or 1.

Additional preferred compounds are those in the following tables:

TABLE 1

| $R^1$ | $R^2$ | $R^3$ |
|---|---|---|
| $CF_3$ | Cl | 4-Cl—Ph |
| $OCF_3$ | Cl | $CO_2Me$ |
| $CF_3$ | Cl | $CO_2Me$ |
| Br | Cl | $CO_2Me$ |
| Cl | Cl | $CO_2Me$ |
| $OCF_3$ | F | 4-F—Ph |
| Cl | F | 4-F—Ph |
| Br | F | 4-F—Ph |
| $OCF_3$ | Cl | Me |
| Br | Cl | Me |
| $OCF_3$ | Cl | n-Pr |
| Br | Cl | n-Pr |
| Cl | Cl | n-Pr |
| $OCF_3$ | $CF_3$ | $CO_2Me$ |
| Cl | $CF_3$ | $CO_2Me$ |
| $CF_3$ | F | $CO_2Me$ |
| Br | F | $CO_2Me$ |
| Cl | F | $CO_2Me$ |
| $OCF_3$ | F | $CO_2Me$ |
| Br | F | Ph |
| $OCF_3$ | F | Ph |
| $CF_3$ | F | 4-F—Ph |
| $OCF_3$ | F | Et |
| $CF_3$ | F | Et |
| $OCF_3$ | F | Me |
| $CF_3$ | F | Me |
| $OCF_3$ | Cl | $CO_2Et$ |
| $CF_3$ | $CF_3$ | $CO_2Me$ |
| Cl | F | Me |

TABLE 2

| $R^1$ | $R^2$ | $R^3$ | $R^4$ | Y |
|---|---|---|---|---|
| $OCF_3$ | Cl | $CO_2Me$ | H | Me |
| $OCF_3$ | Cl | $CO_2Me$ | Me | H |
| $OCF_3$ | Cl | $CO_2Me$ | H | $CO_2Me$ |
| $OCF_3$ | Cl | $CO_2Me$ | H | $CO_2Me$ |
| Br | F | 4-F—Ph | H | Me |

TABLE 2-continued

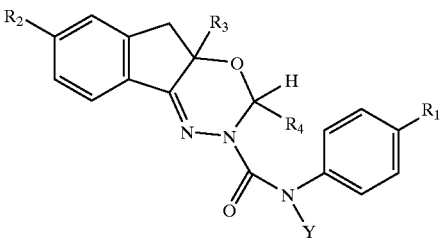

| R¹ | R² | R³ | R⁴ | Y |
|---|---|---|---|---|
| Br | F | 4-F—Ph | H | CO₂Me |
| Br | F | 4-F—Ph | H | CO₂Me |
| Br | F | 4-F—Ph | Me | H |
| Br | F | 4-F—Ph | Et | H |
| OCF₃ | Cl | CO₂Me | Et | H |
| CF₃ | F | CO₂Me | Me | H |
| OCF₃ | F | CO₂Me | Me | H |
| OCF₃ | F | 4-F—Ph | Et | H |
| OCF₃ | F | 4-F—Ph | Me | H |
| Br | Cl | CO₂Me | H | Me |
| CF₃ | Cl | CO₂Me | H | Me |
| CF₃ | F | CO₂Me | Et | H |
| CF₃ | Cl | CO₂Me | H | CO₂Me |
| Br | Cl | CO₂Me | H | CO₂Me |
| OCF₃ | F | CO₂Me | H | Me |
| CF₃ | F | CO₂Me | H | Me |
| OCF₃ | Cl | CO₂Et | H | Et |
| OCF₃ | Cl | CO₂Me | H | Et |
| CF₃ | Cl | CO₂Et | H | Et |
| CF₃ | Cl | CO₂Me | H | Et |
| OCF₃ | Cl | CO₂Me | H | CO₂Et |
| Br | F | 4-F—Ph | H | CO₂Et |
| Br | F | 4-F—Ph | H | Et |
| Br | F | 4-F—Ph | H | COMe |
| OCF₃ | Cl | CO₂Et | H | Me |
| OCF₃ | F | 4-F—Ph | H | CO₂Et |
| OCF₃ | F | 4-F—Ph | H | Et |
| Br | F | 4-F—Ph | H | CH₂SMe |

TABLE 3

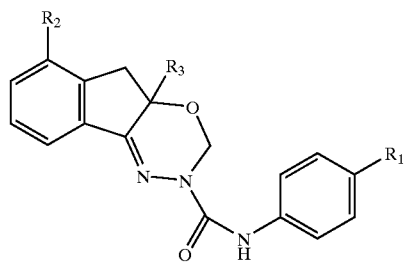

| R¹ | R² | R³ |
|---|---|---|
| OCF₃ | F | 4-F—Ph |
| OCF₃ | Cl | 4-F—Ph |
| OCF₃ | F | Me |

TABLE 4

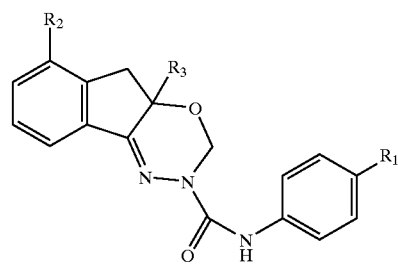

| R¹ | R² | R³ | Y |
|---|---|---|---|
| OCF₃ | Cl | Me | H |
| CF₃ | Cl | Me | H |
| CF₃ | Cl | Et | H |
| CF₃ | F | Et | H |
| OCF₃ | F | Et | H |
| OCF₃ | Cl | CO₂Me | H |
| CF₃ | Cl | CO₂Me | H |
| Br | Cl | CO₂Me | H |
| Cl | Cl | CO₂Me | H |
| OCF₃ | F | CO₂Me | H |
| CF₃ | F | CO₂Me | H |
| Br | F | CO₂Me | H |
| Cl | F | CO₂Me | H |
| OCF₃ | Cl | CO₂Me | Me |
| CF₃ | Cl | CO₂Me | Me |
| Br | Cl | CO₂Me | Me |

TABLE 5

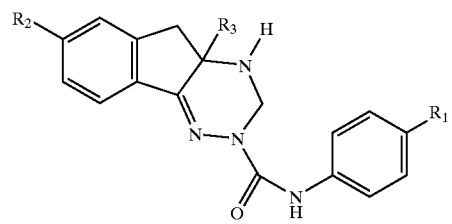

| R¹ | R² | R³ |
|---|---|---|
| OCH₃ | Cl | CO₂CH₃ |

TABLE 6

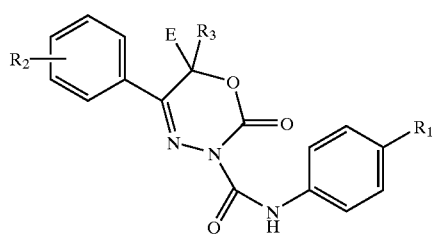

| R¹ | R² | R³ | E |
|---|---|---|---|
| H | H | Ph | H |

Unless otherwise specified, alkyl and alkoxy groups have from one to four carbon atoms. The haloalkyl and haloalkoxy groups likewise preferably have one to four carbon atoms. The various individual aliphatic hydrocarbon moieties, that is, radicals and portions thereof (for example the alkyl moiety of alkylaminocarbonyl and alkylaminosulfonyl), have up to four carbon atoms in the chain.

The haloalkyl and haloalkoxy groups can bear one or more halogen atoms.

The term heteroaryl refers to a five to seven membered heterocyclic ring containing from one to four heteroatoms selected from nitrogen, oxygen and sulfur.

In the above definitions, the term "alkyl" used either alone or in compounds words such as "alkylthio" or "haloalkyl," denotes straight chain or branched alkyl, such as methyl, ethyl, n-propyl, isopropyl or the different butyl, pentyl, hexyl isomers. Alkoxy denotes methoxy, ethoxy, n-propyloxy, isopropyloxy and the different butoxy or pentoxy isomers. Alkenyl denotes straight chain or branched alkenes, such as vinyl, 1-propenyl, 2-propenyl, 3-propenyl and the different butenyl, pentenyl and hexenyl isomers. Alkynyl denotes straight chain or branched alkynes, such as ethynyl, 1-propynyl, 3-propynyl and the different butynyl, pentynyl and hexynyl isomers. Alkylthio denotes methylthio, ethylthio and the different propylthio, butylthio, pentylthio and hexylthio isomers. Alkylsulfinyl, alkylsulfonyl, alkylamino, and the like are defined analogously to the above examples. Cycloalkyl denotes cyclopropyl, cyclobutyl, cyclopentyl and cyclohexyl.

The term "halogen," either alone or in compound words such as "haloalkyl," denotes fluorine, chlorine, bromine or iodine. Further, when used in compound words such as "haloalkyl," said alkyl may be partially or fully substituted with halogen atoms, which may be the same or different. Examples of haloalkyl include $CH_2$ $CH_2$ F, $CF_2$ $CF_2$ and $CH_2$ CHFCl. The terms "halocycloalkyl," "haloalkenyl" and "haloalkynyl" are defined analogously to the term "haloalkyl".

The total number of carbon atoms in a substituent group is indicated by the "$C_i$-$C_j$" prefix where I and j are numbers from 1 to 8. For example, $C_1$-$C_3$ alkylsulfonyl designates methylsulfonyl through propylsulfonyl; $C_2$ alkoxyalkoxy designates $OCH_2$ $OCH_3$; $C_4$ alkoxyalkoxy designates the various isomers of an alkoxy group substituted with a second alkoxy group containing a total of 4 carbon atoms, examples including $OCH_2$ $OCH_2$ $CH_2$ $CH_3$ and $OCH_2$ $CH_2$ $OCH_2$ $CH_3$; $C_2$ cyanoalkyl designates $CH_2$ CN and $C_3$ cyanoalkyl designates $CH_2$ $CH_2$ CN and $CH(CN)CH_3$; $C_2$ alkylcarbonyl designates $C(O)CH_3$ and $C_4$ alkylcarbonyl includes $C(O)CH_2$ $CH_2$ $CH_3$ and $C(O)CH(CH_3)_2$ ; $C_2$ alkoxycarbonyl designates $C(O)OCH_3$ and $C_4$ alkoxycarbonyl designates $C(O)OCH_2$ $CH_2$ $CH_3$ and $C(O)OCH(CH_3)_2$; and as a final example, $C_3$ alkoxycarbonylalkyl designates $CH_2$ $CO_2$ $CH_3$ and $C_4$ alkoxycarbonylalkyl includes $CH_2$ $CH_2$ $CO_2$ $CH_3$, $CH_2$ $CO_2$ $CH_2$ $CH_3$ and $CH(CH_3)CO_2$ $CH_3$.

Preferably, the compounds are indoxacarb and ethiprole. In a preferred embodiment, the compositions and methods are used for treating rice crops. Various insects can be controlled using the compositions described herein by applying an effective amount of the compositions to the plants or to the medium in which they grow.

DETAILED DESCRIPTION OF THE INVENTION

The present invention is directed to compositions and methods for controlling insect populations. The compositions include one or more compounds from Formula 1A and one or more compounds from Formulas 1B–G described above, where the compounds preferably include indoxacarb and ethiprole, in at least an amount effective to control populations of *Nilaparvata lugens* (brown planthoppers), *Cnaphalocrocis medinalis* (rice leaf rollers) and Nephotettix spp. (rice leaf hoppers), for example, *Nephotettix cincticeps* (green leaf hopper), when applied to rice crops. In some embodiments, a synergistic effect is observed between the indoxacarb and the ethiprole with respect to their ability to control populations of Nephotettix spp. Synergy tends to be observed when the composition is applied to the insects as well as the plants. Synergy does not tend to be observed when the composition is applied only to the plants and then untreated insects are introduced to the treated plants.

I. Insecticidal Compositions

The compositions include one or more compounds of Formula 1A and one or more compounds of Formulas 1B–G. The compounds are preferably indoxacarb and ethiprole, and are preferably present in an amount which provides for synergistic effects with respect to controlling *Nephotettix cincticeps* (green leaf hopper). When used in connection with the protection of rice crops from insect infestation, the compositions are advantageous in that they allow application of a single composition to control all of the major insects which attack rice crops, namely, *Nilaparvata lugens* (brown planthoppers), *Cnaphalocrocis medinalis* (rice leaf rollers) and Nephotettix spp. (rice leaf hoppers), for example, *Nephotettix cincticeps* (green leaf hopper).

The compositions usually contain from 0.00005% to 90%, more preferably from 0.001% to 40% by weight of total active ingredients, and optionally include other insecticides, suitable carriers, anthelmintics, anticoccidials, synergists, trace elements, stabilizers, and other components commonly found in insecticidal compositions.

The actual compositions employed and their rate of application will be selected to achieve the desired effect(s) by the farmer, livestock producer, medical or veterinary practitioner, pest control operator other person skilled in the art. Solid and liquid compositions for application topically to animals, timber, stored products or household goods preferably contain from 0.00005% to 90%, more preferably from 0.001% to 40%, by weight of the active compounds.

Dusts and liquid compositions for application to livestock, persons, goods, premises or outdoor areas may contain 0.00005% to 90%, and more preferably 0.001% to 40%, by weight of the active compounds, which are preferably ethiprole and indoxacarb.

The compositions can be used to control pests which feed on parts of the plant remote from the point of application, e.g., leaf feeding insects can be killed by the subject compounds applied to roots. Alternatively, the compounds can be applied by foliar application. In one embodiment, ethiprole and/or related compounds are applied to the roots, and indoxacarb or related compounds are applied as a foliar spray. In addition, the compounds may reduce attacks on the plant by means of antifeeding or repellent effects.

A. Indoxacarb

Indoxacarb by itself is not particularly active against *Nilaparvata lugens* (brown planthoppers), but is very active against *Cnaphalocrocis medinalis* (rice leaf rollers). It has some activity by itself against *Nephotettix cincticeps* (green leaf hoppers), but the activity tends to be slow. The activity of indoxacarb against *Nephotettix cincticeps* tends to be speeded up by the addition of ethiprole. Further, the overall toxicity of indoxacarb tends to be increased by the addition of ethiprole. The chemical formula for indoxacarb is:

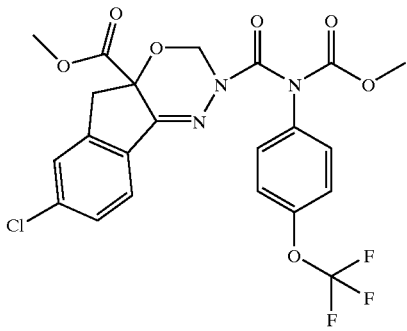

B. Ethiprole

Ethiprole is not particularly active against *Cnaphalocrocis medinalis* (rice leaf rollers), but shows activity against *Nilaparvata lugens* (brown planthoppers). It has some activity by itself against *Nephotettix cincticeps* (green leaf hoppers). The chemical formula for ethiprole is:

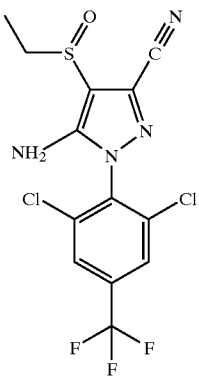

With respect to controlling populations of *Nephotettix cincticeps* (green leaf hoppers), synergy is observed when the ethiprole and indoxacarb were applied in ratios of between 2:1 and 32:1 by weight. This effect is surprising, since neither ethiprole nor indoxacarb are particularly effective alone at controlling this type of insect.

C. Other Insecticides

The compositions can include other insecticides in addition to the compounds of Formulas 1A–G, which are preferably ethiprole and indoxacarb. Suitable insecticides include fipronil, acephate, chlorpyrifos, demeton-S-methyl, disulfoton, ethoprofos, fenitrothion, malathion, monocrotophos, parathion, phosalone, pirimiphos-methyl, triazophos, cyfluthrin, cypermethrin, deltamethrin, fenpropathrin, fenvalerate, permethrin, aldicarb, carbosulfan, methomyl, oxamyl, pirimicarb, bendiocarb, teflubenzuron, dicofol, endosulfan, lindane, benzoximate, cartap, cyhexatin, tetradifon, avermectins, ivermectin, milbemycins, thiophanate, trichlorfon, dichlorvos, diaveridine, spinosad and dimetridazole, although those of skill in the art are aware of numerous other useful insecticides.

D. Optional Additional Components

The compositions may include, if appropriate, suitable carriers, anthelmintics, anticoccidials, synergists, trace elements, stabilisers, adhesives, wetting agents, dispersants, emulsifiers, penetrants, solvents, fillers and/or carriers which are conventional in each case.

Compositions in the form of aerosols and aqueous or non-aqueous solutions or dispersions suitable for spraying, fogging and low- or ultra-low volume spraying may be used. Suitable solid diluents which may be used in the preparation of compositions suitable for applying the compositions include aluminum silicate, kieselguhr, corn husks, tricalcium phosphate, powdered cork, absorbent carbon black, magnesium silicate, a clay such as kaolin, bentonite or attapulgite, and water soluble polymers and such solid compositions may, if desired, contain one or more compatible wetting, dispersing, emulsifying or colouring agents which, when solid, may also serve as diluent.

Such solid compositions, which may take the form of dusts, granules or wettable powders, are generally prepared by impregnating the solid diluents with solutions of the compositions in volatile solvents, evaporating the solvents and, if necessary, grinding the products so as to obtain powders and, if desired, granulating or compacting the products so as to obtain granules, pellets or briquettes or by encapsulating finely divided active ingredient in natural or synthetic polymers, e.g., gelatin, synthetic resins and polyamides.

The wetting, dispersing and emulsifying agents which may be present, particularly in wettable powders, may be of the ionic or non-ionic types, for example sulphoricinoleates, quaternary ammonium derivatives or products based upon condensates of ethylene oxide with nonyl- and octylphenol, or carboxylic acid esters of anhydrosorbitols which have been rendered soluble by etherification of the free hydroxy groups by condensation with ethylene oxide, or mixtures of these types of agents. Wettable powders may be treated with water immediately before use to give suspensions ready for application.

Liquid compositions for the application of the compositions may take the form of solutions, suspensions and emulsions of the compositions optionally encapsulated in natural or synthetic polymers, and may, if desired, incorporate wetting, dispersing or emulsifying agents. These emulsions, suspensions and solutions may be prepared using aqueous, organic or aqueous-organic diluents, for example acetophenone, isophorone, toluene, xylene, mineral, animal or vegetable oils, and water soluble polymers (and mixtures of these diluents), which may contain wetting, dispersing or emulsifying agents of the ionic or non-ionic types or mixtures thereof, for example those of the types described above. When desired, the emulsions containing the compositions may be used in the form of self-emulsifying concentrates containing the active substance dissolved in the emulsifying agents or in solvents containing emulsifying agents compatible with the active substance, the simple addition of water to such concentrates producing compositions ready for use.

The compositions, when applied to control arthropod, plant nematode, helminth or protozoan pests, may also contain synergists (e.g. piperonyl butoxide or sesamex), stabilizing substances, other insecticides, acaricides, plant nematocides, anthelmintics or anticoccidials, fungicides (agricultural or veterinary as appropriate e.g. benomyl, iprodione), bactericides, arthropod or vertebrate attractants or repellents or pheromones, reodorants, flavoring agents, dyes and auxiliary therapeutic agents, e.g., trace elements. These may be designed to improve potency, persistence, safety, uptake where desired, spectrum of pests controlled or to enable the composition to perform other useful functions in the same animal or area treated.

E. Formulations Including the Compositions Described Herein

The mixing ratios of the ethiprole and indoxacarb can vary within wide limits, depending on numerous factors, including the relative populations of the insects to be controlled. However, it is preferred that the ethiprole and indoxacarb are present in an amount which provides for a synergistic effect with respect to controlling Nephotettix spp. The compositions can also include suitable formulation auxiliaries.

The compositions can exist not only as mixed formulations of the two components which are then diluted with water in the customary manner or applied as granules, but also in the form of so-called tank mixes by jointly diluting the components, which are formulated separately, with water.

Based on these formulations, it is also possible to prepare combinations with other pesticidally active substances, such as selective herbicides and specific fungicides or insecticides, and also fertilizers and/or growth regulators, for example in the form of a readymix or a tank mix.

The components can be formulated in a variety of ways. Suitable formulation options are, for example: yeast formulations, starch formulations, wettable powders (WP), emulsifiable concentrates (EC), aqueous solutions (SL), emulsions (EW) such as oil-in-water and water-in-oil emulsions, sprayable solutions or emulsions, oil- or water-based dispersions, suspoemulsions, dusts (DP), seed treatment products, granules for soil or paddy application or spreading, or water-dispersible granules (WG), ULV formulations, microcapsules or baits (substrates). Oil-in-water and water-in-oil emulsions, wettable powders or granules are of particular interest.

These individual formulation types are known in principle and are described, for example, in: Winnacker-Kuchler, "Chemische Technologie" *Chemical Technology,* Vol. 7, C. Hauser Verlag Munich, 4th Ed. 1986; van Valkenburg, "Pesticide Formulations", Marcel Dekker N.Y., 2nd Edition 1972–73; K. Martens, "Spray Drying Handbook", 3rd Edition, G. Goodwin Ltd. London.

The formulation auxiliaries required, such as inert materials, surfactants, solvents and other additives, are also known and are described, for example, in: Watkins, *Handbook of Insecticide Dust Diluents and Carriers,* 2nd Edition, Darland Books, Caldwell N.J.; H. V. Olphen, *Introduction to Clay Colloid Chemistry,* 2nd Edition, J. Wiley & Sons, N.Y., Marsden, *Solvents Guide,* 2nd Edition, Interscience, N.Y. 1950; McCutcheon's, "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schonfeldt, "Grenzflachenaktive Athylenoxidaddukte" Surface-active Ethylene Oxide Adducts, Wiss. Verlagsgesell., Stuttgart 1976; Winnacker-Kuchler, "Chemische Technologie" *Chemical Technology,* Vol. 7, C. Hauser Verlag Munich, 4th Ed. 1986.

Wettable powders are preparations which are uniformly dispersible in water and which, besides the active substance, also comprise wetting agents, for example polyoxyethylated alkylphenols, polyoxyethylated fatty alcohols or fatty amines, alkane sulfonates or alkylbenzene sulfonates, and dispersants, for example sodium lignosulfonate, sodium 2,2'-dinaphthylmethane-6,6'-disulfonate, sodium dibutylnaphthalene sulfonate, or else sodium oleoylmethyltaurinate, in addition to a diluent or inert substance.

Emulsifiable concentrates can be prepared by dissolving the active substance in an organic solvent, for example butanol, cyclohexanone, dimethylformamide, xylene, or else higher-boiling aromatic compounds or hydrocarbons, with the addition of one or more emulsifiers. Examples of emulsifiers which can be used are: calcium alkylarylsulfonates, such as calcium dodecylbenzenesulfonate, or non-ionic emulsifiers, such as fatty acid polyglycol esters, alkylaryl polyglycol ethers, fatty alcohol polyglycol ethers, propylene oxide/ethylene oxide condensates, alkyl polyethers, sorbitan fatty acid esters, polyoxyethylene sorbitan fatty acid esters or polyoxyethylene sorbitol esters.

Dusts can be obtained by grinding the active substance with finely divided solid substances, for example talc, natural clays, such as kaolin, bentonite and pyrophyllite, or diatomaceous earth. Granules can be produced either by spraying the active substance onto adsorptive, granulated inert material or by applying active substance concentrates to the surface of carriers, such as sand, kaolinites or granulated inert material, by means of binders, for example polyvinyl alcohol, sodium polyacrylate or, alternatively, mineral oils. Suitable active substances can also be granulated in the manner which is conventional for the production of fertilizer granules, if desired in a mixture with fertilizers.

As a rule, the agrochemical preparations comprise 0.0001 to 99 percent by weight, in particular between 0.0005 and 95%, particularly preferably between 2 and 90%, of the active components, for example, ethiprole and indoxacarb.

The concentration of active substance in wettable powders is, for example, about 10 to 90% by weight; the remainder to 100% by weight is composed of conventional formulation components. In the case of emulsifiable concentrates, the concentration of active substance can be about 1 to 90% by weight, preferably 5 to 80% by weight. Formulations in the form of dusts comprise about 1 to 30% by weight, preferably 5 to 20% by weight, of active substance, sprayable solutions about 0.05 to 80% by weight, preferably 2 to 50% by weight, of active substance. In the case of granules, for example water-dispersible granules, the active substance content depends partly on whether the active compound is in liquid or solid form and on which granulation auxiliaries and fillers are used. As a rule, water-dispersible granules comprise between 1 and 95% by weight, granules for spreading between 1 and 50%, preferably between 2 and 25%. Baits have an active substance content of between 0.0001 and 10% as regards the active compounds, for example, ethiprole and indoxacarb. The use concentration can vary between 0.1 ppm (0.0001 g/l) and 10,000 ppm (10 g/l), preferably between 0.5 and 5,000 ppm, particularly preferably between 5 and 1,000 ppm.

II. Insects Which can be Treated

Preferably, the compositions are used to treat rice crops for pests such as *Nilaparvata lugens* (brown planthoppers), *Cnaphalocrocis medinalis* (rice leaf rollers), and Nephotettix spp. (rice leaf hoppers), for example, *Nephotettix cincticeps* (green leaf hopper) the most common pests to attack rice crops.

The compositions described herein can generally be used to control arthropod, plant nematode, helminth or protozoan pests at a locus by treating the locus (for example, by application or administration) with an effective amount of the compositions. The compositions may, in particular, be used in the field of veterinary medicine and livestock husbandry and in the maintenance of public health against arthropods, helminths or protozoa which are parasitic internally or externally upon vertebrates, particularly warm-blooded vertebrates, for example man and domestic animals, e.g. cattle, sheep, goats, equines, swine, poultry, dogs, cats and fishes, for example Acarina, including fleas, ticks (e.g. Ixodes spp., Boophilus spp. e.g. *Boophilus microplus,* Amblyomma spp., Hyalomma spp., Rhipicephalus spp. e.g. *Rhipicephalus appendiculatus,* Haemaphysalis spp., Dermacentor spp., Ornithodorus spp. (e.g. *Ornithodorus moubata* and mites (e.g. Damalinia spp., *Dermahyssus gallinae,* Sarcoptes spp. e.g. *Sarcoptes scabiei,* Psoroptes Spp. Chorioptes spp., Demodex spp., Eutrombicula spp.); Diptera (e.g. Aedes spp., Anopheles spp., Musca spp., Hypoderma spp., Gasterophilus spp., Simulium spp.); Hemiptera (e.g. Triatoma spp.); Phthiraptera (e.g. Damalinia spp., Linognathus spp.); Siphonapters (e.g. Ctenocephalides spp.); Dictyoptera (e.g. Periplaneta spp., Blatella spp.); Hymenoptera (e.g. *Monomorium pharaonis*); for example against infections of the gastrointestinal tract caused by parasitic nematode worms, for example members of the family Trichostrongylidae, *Nippostrongylus brasiliensis, Trichinella spiralis, Haemonchus contortus, Trichostrongylus colubriformis, Nematodirus battus, Ostertagia circumcincta, Trichostrongylus axei,* Cooperia spp. and *Hymenolepis nana;* in the control and treatment of protozoal diseases caused by, for example, Eimeria spp. e.g. *Eimeria tenella, Eimeria acervulina, Eimeria brunetti, Eimeria maxima* and *Eimeria necatrix, Trypanosoma cruzi,* Leishmania spp., Plasmodium spp., Babesia spp., Trichomonadidae spp., Histomonas spp., Giardia spp., Toxoplasma spp., *Entamoeba histolytica* and Theileria spp.; in the protection of stored products, for example cereals, including grain and flour, groundnuts, animal feedstuffs, timber and household goods, e.g. carpets and textiles, against attack by arthropods, more especially beetles, including weevils, moths and mites, for example Ephestia spp. (flour moths), Anthrenus spp. (carpet beetles), Tribolium spp. (flour beetles), Sitophilus spp. (grain weevils) and Acarus spp. (mites), to control cockroaches, silverfish, spiders, ants and termites and similar arthropod pests in infested domestic and industrial premises and in the control of mosquito larvae in waterways, wells, reservoirs or other running or standing water; for the treatment of foundations, structure and soil in the prevention of the attack on buildings by termites, for example, Reticulitermes spp., Heterotermes spp., Coptotermes spp.; in agriculture, against adults, larvae and eggs of Lepidoptera (butterflies and moths), e.g. Heliothis spp. such as *Heliothis virescens* (tobacco budworm), *Heliothis armigera* and *Heliothis zea,* Spodoptera spp. such as *S. exempta, S. littoralis* (Egyptian cotton worm), *S. eridania* (southern army worm), *Mamestra configurata* (bertha army worm); Earias spp. e.g. *E. insulana* (Egyptian bollworm), Pectinochora spp. e.g. *Pectinophora gossypiella* (pink bollworm), Ostrinia spp. such as *O. nubilalis* (European cornborer), *Trichoplusia ni* (cabbage looper), Pieris spp. (cabbage worms), Laphygma spp. (army worms), Agrotis and Amathes spp. (cutworms), Wiseana spp. (porina moth), Chilo spp. (rice stem borer), Tryporyza spp. and Diatraea spp. (sugar cane borers and rice borers), *Sparganothis pilleriana* (grape berry moth), *Cydia pomonella* (codling moth), Archips spp. (fruit tree tortrix moths), *Plutella xylostella* (diamond back moth); against adult and larvae of Coleoptera (beetles) e.g. *Hypothenemus hampei* (coffee berry borer), Hylesinus spp. (bark beetles), *Anthonomus grandis* (cotton boll weevil), Acalymma spp. (cucumber beetles), Lema spp., Psylliodes spp., *Leptinotarsa decemlineata* (Colorado potato beetle), Diabrotica spp. (corn rootworms), Gonocephalum spp. (false wire worms) Agriotes spp. (wireworms), Dermolepida and Heteronychus spp. (white grubs), *Phaedon cochleariae* (mustard beetle), *Lissorhoptrus oryzophilus* (rice water weevil), Meligethes spp. (pollen beetles), Ceutorhynchus spp., Rhynchophorus and Cosmopolites spp. (root weevils); against Hemiptera e.g. Psylla spp., Bemisia spp., Trialeurodes spp., Aphis spp., Myzus spp., *Megoura viciae,* Phylloxera spp., Adelges spp., *Phorodon humuli* (hop damson aphid), Aeneolamia spp., Nephotettix spp. (rice leaf hoppers), Empoasca spp., Nilaparvata spp., Perkinsiella spp., Pyrilla spp., Aonidiella spp. (red scales), Coccus spp., Pseucoccus spp., Helopeltis spp. (mosquito bugs), Lygus spp., Dysdercus spp., Oxycarenus spp., Nezara spp.; Hymenoptera e.g. Athalia spp. and Cephus spp. (saw flies), Atta spp. (leaf cutting ants); Diptera e.g. Hylemyia spp. (root flies), Atherigona spp. and Chlorops spp. (shoot flies), Phytomyza spp. (leaf miners), Ceratitis spp. (fruit flies); Thysanoptera such as *Thrips tabaci;* Orthoptera such as Locusta and Schistocerca spp. (locusts) and crickets e.g. Gryllus spp. and Acheta spp.; Collembola e.g. Sminthurus spp. and Onychiurus spp. (springtails), Isoptera e.g. Odontotermes spp. (termites), Dermaptera e.g. Forficula spp. (earwigs) and also other arthropods of agricultural significance such as Acari (mites) e.g. Tetranychus spp., Panonychus spp. and Bryobia spp. (spider mites), Eriophyes spp. (gall mites), Polyphacotarsonemus spp.; Blaniulus spp. (millipedes), Scutigerella spp. (symphilids), Oniscus spp. (woodlice) and Triops spp. (crustacea); nematodes which attack plants and trees of importance to agriculture, forestry and horticulture either directly or by spreading bacterial, viral, mycoplasma or fungal diseases of the plants, root-knot nematodes such as Meloidogyne spp. (e.g. *M. incognita*); cyst nematodes such as Globodera spp. (e.g. *G. rostochiensis*); Heterodera spp. (e.g. *H. avenae*); Radopholus spp. (e.g. *R. similis*); lesion nematodes such as Pratylenchus spp. (e.g. *P. pratensis*); Belonolaimus spp. (e.g. *B. gracilis*); Tylenchulus spp. (e.g. *T. semipenetrans*); Rotylenchulus spp. (e.g. *R. reniformis*); Rotylenchus spp. (e.g. *R. robustus*); Helicotylenchus spp. (e.g. *H. multicinctus*); Hemicycliophora spp. (e.g. *H. gracilis*); Criconemoides spp. (e.g. *C. similis*); Trichodorus spp. (e.g. *T. primitivus*); dagger nematodes such as Xiphinema spp. (e.g. *X diversicaudatum*), Longidorus spp. (e.g. *L. elongatus*); Hoplolaimus spp. (e.g. *H. coronatus*); Aphelenchoides spp. (e.g. *A. ritzema-bosi, A. besseyi*); stem and bulb eelworms such as Ditylenchus spp. (e.g. *D. dipsaci*).

The compositions can also be used to treat humans infected with, for example, Head lice (*Pediculus humanus capitis*) and body lice (*Pediculus humanus humanus*).

III. Plant Varieties Which can be Protected Using the Compositions Described Herein The compositions can be used to protect cereal crops (such as maize, wheat, rice, sorghum), in particular rice crops, and can also be used in connection with field, forage, plantation, glasshouse, orchard and vineyard crops, of ornamentals and of plantation and forest trees, for example, cotton, tobacco, vegetables and salads (such as beans, cole crops, curcurbits, lettuce, onions, tomatoes and peppers), field crops (such as potato, sugar beet, ground nuts, soyabean, oil seed rape), sugar cane, grassland and forage (such as maize, sorghum, lucerne), plantations (such as of tea, coffee, cocoa, banana, oil palm, coconut, rubber, spices), orchards and groves (such as of stone and pip fruit, citrus, kiwifruit, avocado, mango, olives and walnuts), vineyards, ornamental plants, flowers and shrubs under glass and in gardens and parks, forest trees (both deciduous and evergreen) in forests, plantations and nurseries.

The compositions can also be used to protect timber (standing, felled, converted, stored or structural) from attack by sawflies (e.g. Urocerus) or beetles (e.g. scolytids, platypodids, lyctids, bostrychids, cerambycids, anobiids), or termites, for example, Reticulitermes spp., Heterotermes spp., Coptotermes spp.

The compositions can also be used to protect stored products such as grains, fruits, nuts, spices and tobacco, whether whole, milled or compounded into products, from moth, beetle and mite attack. Also protected are stored animal products such as skins, hair, wool and feathers in natural or converted form (e.g. as carpets or textiles) from moth and beetle attack; also stored meat and fish from beetle, mite and fly attack.

IV. Methods of Controlling Insects

To control arthropods and nematodes, the compositions are generally applied to the locus in which arthropod or nematode infestation is to be controlled at a rate of about 0.00001 kg to about 20 kg per hectare of locus treated. Under ideal conditions, depending on the pest to be controlled, the lower rate may offer adequate protection. On the other hand, adverse weather conditions, resistance of the pest and other factors may require that the active ingredient be used in higher proportions. In foliar application, a rate of 0.0001 g/ha to 1000 g/ha may be used.

When the pest is soil-borne, the composition is distributed evenly over the area to be treated in any convenient manner. Application may be made, if desired, to the field or crop-growing area generally or in close proximity to the seed or plant to be protected from attack. The active component can be washed into the soil by spraying with water over the area or can be left to the natural action of rainfall. During or after application, the formulation can, if desired, be distributed mechanically in the soil, for example by ploughing or disking. Application can be prior to planting, at planting, after planting but before sprouting has taken place or after sprouting.

The composition may be applied in solid or liquid compositions to the soil principally to control those nematodes dwelling therein but also to the foliage principally to control those nematodes attacking the aerial parts of the plants (e.g. Aphelenchoides spp. and Ditylenchus spp. listed above).

Suitable means of applying the compositions to growing crops include foliar sprays, dusts, granules, fogs and foams; also as suspensions of finely divided particles; as soil and root treatments by liquid drenches, dusts, granules, smokes and foams; and as seed dressings by liquid slurries and dusts.

Among the cultivated plants, the methods described herein are most particularly effective in rice plants cultivated in a paddy field.

As will be well understood to those of skill in the art, the application rate of the composition will be expected to vary with the external conditions, for example, temperature, humidity and the like, as well as the particular field of application and on the plant to be treated. Accordingly, it can vary within wide limits.

The two major components, which are the at least one compound from Formula 1A and at least one compound from Formulas 1B–G, and which are preferably ethiprole and indoxacarb, can be applied simultaneously or in succession. However, for ease of application, it is preferred that the composition which is applied to the plants include both components.

The present invention will be better understood with reference to the following non-limiting examples.

EXAMPLE 1

Activity of the Compositions Against *Nephotettix cincticeps* (Green Leaf Hopper), *Nilaparvata lugens* (Brown Planthoppers) and *Cnaphalocrocis medinalis* (Rice Leaf Rollers)

In experiments on activity against Nephotettix spp. (rice leaf hoppers), for example, *Nephotettix cincticeps* (green leaf hopper), carried out on representative compounds of the first preferred embodiment, the following results (wherein ppm indicates the concentration of the compound in parts per million of the test solution applied) have been obtained, as shown in Table 7:

TABLE 7

*Nephotettix cincticeps* Results

| | | % mortality Indoxacarb (ppm) | | |
|---|---|---|---|---|
| | 0 | 6.25 | 12.5 | 25 |
| Ethiprole | 0 | 0.0 | 0.0 | 16.2 | 38.0 |
| (ppm) | 200 | 0.0 | 37.8 | 66.2 | 96.0 |

As shown in the table, Indoxacarb at 25 ppm results in a 38% kill, and Ethiprole at 200 ppm results in a 37.8% kill. The combination provides significantly more kill (96.0%) wthan either Ethiprole or Indoxacarb alone.

We claim:

1. An insecticidal composition comprising synergistically insecticidal effective amounts of ethiprole and indoxacarb, wherein the ratio by weight of ethiprole to indoxacarb is between 1:32 and 32:1.

2. The composition of claim 1, further comprising a carrier.

3. The composition of claim 1, further comprising an additional insecticide.

4. The composition of claim 1, wherein the composition is in the form of a conventional crop protection product formulation selected from the group consisting of wettable powders, emulsifiable concentrates, aqueous solutions, emulsions, sprayable solutions, oil- or water-based dispersions, suspoemulsions, dusts, seed treatment products, granules for soil application or spreading, water-dispersible granules, ULV formulations, microcapsules and waxes.

5. The composition of claim 1, wherein the composition comprises 10 to 80% by weight of ethiprole and indoxacarb.

6. The composition of claim 5, wherein the composition comprises between 10 and 50% by weight of ethiprole and indoxacarb.

7. The composition of claim 1, wherein the ratio by weight of ethiprole to indoxacarb is between 2:1 and 32:1.

8. The composition of claim 7, further comprising a carrier.

9. The composition of claim 7, further comprising an additional insecticide.

10. The composition of claim 7, wherein the composition is in the form of a conventional crop protection product formulation selected from the group consisting of wettable powders, emulsifiable concentrates, aqueous solutions, emulsions, sprayable solutions, oil- or water-based dispersions, suspoemulsions, dusts, seed treatment products, granules for soil application or spreading, water-dispersible granules, ULV formulations, microcapsules and waxes.

11. The composition of claim 7, wherein the composition comprises 10 to 80% by weight of ethiprole and indoxacarb.

12. The composition of claim 7, wherein the composition comprises between 10 and 50% by weight of ethiprole and indoxacarb.

13. A method of controlling infestation of insect pests in or on rice plants, comprising applying an insecticidal composition to the insect pests, to the rice plants, to medium in which the rice plants grow, and/or to a locus in which infestation is to be controlled, wherein the composition comprises synergistically insecticidal effective amounts of ethiprole and indoxacarb and wherein the ratio by weight of ethiprole to indoxacarb is between 1:32 and 32:1.

14. The method of claim 13, wherein the ratio by weight of ethiprole to indoxacarb in the composition is between 2:1 and 32:1.

15. The method of claim 13, wherein the composition further comprises a carrier.

16. The method of claim 13, wherein the composition further comprises an additional insecticide.

17. The method of claim 13, wherein the composition is in the form of a conventional crop protection product formulation selected from the group consisting of wettable powders, emulsifiable concentrates, aqueous solutions, emulsions, sprayable solutions, oil- or water-based dispersions, suspoemulsions, dusts, seed treatment products, granules for soil application or spreading, water-dispersible granules, ULV formulations, microcapsules and waxes.

18. The method of claim 13, wherein the composition comprises 10 to 80% by weight of ethiprole and indoxacarb.

19. The method of claim 13, wherein the composition comprises between 10 and 50% by weight of ethiprole and indoxacarb.

20. A method of controlling infestation of insect pests in or on rice plants, comprising applying, simultaneously or in succession, synergistically insecticidal effective amounts of ethiprole and indoxacarb to the insect pests, to the rice plants, to medium in which the rice plants grow, and/or to a locus in which infestation is to be controlled, wherein the ratio by weight of ethiprole to indoxacarb applied is between 1:32 and 32:1.

21. The method of claim 20, wherein the ratio by weight of ethiprole to indoxacarb applied is between 2:1 and 32:1.

* * * * *